United States Patent [19]
Gay et al.

[11] Patent Number: 5,332,511
[45] Date of Patent: Jul. 26, 1994

[54] PROCESS OF SANITIZING SWIMMING POOLS, SPAS AND, HOT TUBS

[75] Inventors: Walter A. Gay, Cheshire; Bonnie B. Sandel, Milford; Jayne F. Carney, Wolcott, all of Conn.

[73] Assignee: Olin Corporation, Stamford, Conn.

[21] Appl. No.: 81,899

[22] Filed: Jun. 25, 1993

[51] Int. Cl.$^5$ .............................. C02F 1/50; C02F 1/78
[52] U.S. Cl. .................................... 210/755; 210/760; 210/764; 422/28; 422/37
[58] Field of Search ............... 210/753, 754, 755, 756, 210/764, 760; 252/175, 180, 181; 422/28, 37; 424/630, 632, 634, 637, 638; 514/499, 500, 642

[56] References Cited

U.S. PATENT DOCUMENTS

| | | |
|---|---|---|
| 3,567,729 | 3/1971 | Lewis et al. . |
| 3,624,082 | 11/1971 | Lewis et al. . |
| 3,702,298 | 11/1972 | Zsoldos, Jr. et al. ............... 210/759 |
| 3,730,702 | 5/1973 | Shay et al. . |
| 3,733,420 | 5/1973 | Wakeman et al. . |
| 3,845,216 | 10/1974 | Brink, Jr. et al. ................... 424/329 |
| 4,098,602 | 7/1978 | Seymour et al. . |
| 4,450,174 | 5/1984 | Green et al. ......................... 424/329 |
| 4,569,800 | 2/1986 | Stanley et al. . |
| 4,746,368 | 5/1988 | Frank et al. . |
| 4,806,520 | 2/1989 | Frank et al. . |
| 4,923,619 | 5/1990 | Legros ................................. 210/764 |
| 4,952,398 | 8/1990 | Tapin .................................... 71/67 |
| 5,080,830 | 1/1992 | Damaso . |
| 5,131,938 | 7/1992 | Girvan ................................. 71/67 |
| 5,149,354 | 9/1992 | Delaney . |

FOREIGN PATENT DOCUMENTS

| | | |
|---|---|---|
| 59978 | 6/1984 | European Pat. Off. . |
| 286453A2 | 10/1988 | European Pat. Off. . |
| 2194227 | 3/1988 | United Kingdom . |

OTHER PUBLICATIONS

G. R. Bhat et al., "The Green Hair Problem: A Preliminary Investigation" J. Soc. Cosmet. Chem. 30 (Jan.-/Feb., 1979) (C.A. 90(20):156982r).

Landeen et al., "Efficacy of Copper and Silver Ions and Reduced Levels of Free Chlorine in Inactivation of Legionella Pneumophila"; Applied & Environmental Microbiology, vol. 50, No. 12, Dec., 1989, pp. 3045-3050.

Yahya et al., "Disinfection of Bacteria in Water Systems by Using Electrolytically Generated Copper:Silver & Reduced Levels of Free Chlorine", Can. J. Microbiol. vol. 36, pp. 109-116 (1990).

George P. Fitzgerald, "Compatibility of Swimming Pool Algicides and Bactericides", Water & Sewage Works, vol. 115(2), pp. 65-71 (1968) Federal Register vol. 56, #168, pp. 42,685-42,687, Aug. 29, 1991.

AKZO Product Bulletin for ARQUAD HTL8 (1990).
Stepan Product Bulletin for PTC-99 (1990).

*Primary Examiner*—Neil McCarthy
*Attorney, Agent, or Firm*—William A. Simons

[57] ABSTRACT

A process for sanitizing water in swimming pools, spas and hot tubs whereby the level of bacteria in said water is lowered comprising:

treating said water with a bactericidal effective amount of a combination of di-isodecyl dimethyl ammonium chloride and copper (II) ions, the concentration of diisodecyl dimethyl ammonium chloride in said water being less than about 60 parts per million parts of water by weight; and treating said water at least intermittently with an oxidant selected from the group consisting of available chlorine and ozone.

10 Claims, No Drawings

PROCESS OF SANITIZING SWIMMING POOLS, SPAS AND, HOT TUBS

BACKGROUND OF THE INVENTION

1. Field of the Invention

The present invention relates to a process of sanitizing water in swimming pools, spas, and hot tubs wherein the level of bacteria is lowered. In particular, the present invention relates to a process of sanitizing by treating said water with a bactericidal effective amount of a combination of di-isodecyl dimethyl ammonium chloride and copper (II) ions and also treating said water at least intermittently with an oxidant selected from the group consisting of available chlorine, available bromine and ozone.

2. Brief Description of the Prior Art

Water in swimming pools, spas and hot tubs is constantly recirculated and fresh water is normally added only to maintain the desired volume. Although this water is usually filtered continuously to keep it free of suspended matter, it frequently contains bacteria. Treatment with one or more sanitizers to control the bacteria count is necessary.

Numerous chemical compounds have been reported for use in swimming pools, spas, and hot tubs. These chemicals include various quaternary ammonium salts, copper salts, and oxidants such as chlorine sources or bromine sources or ozone or peroxy compounds such as hydrogen peroxide and potassium peroxymonosulfate (OXONE). The use of combinations of such sanitizers is also known.

At the present time, the main disinfectant used in swimming pools, spas and hot tubs is chlorine. It is an effective bactericide, but suffers from two main disadvantages. One, at improper pH and concentration levels it may cause eye irritation. Two, it has to be added at frequent intervals to maintain an effective concentration for killing bacteria.

Ozone has also been used as a disinfectant for swimming pools, spas and hot tubs; but, it is limited to frequent or continuous dosing to maintain an effective concentration for killing bacteria. Such frequent or continuous treatments are required with ozone since there is at the present time no technology available for providing residual ozone. Also, if people come into contact with high concentrations of ozone, such as where the ozone is injected into the water, they may experience unpleasant headaches and the like.

Certain quaternary ammonium compounds have also been reported as being useful in swimming pools, spas, and hot tubs as bacteristats, bactericides, and algaecides. Those used as bacteristats and bactericides have required relatively high levels (e.g. over 100 ppm by weight) to give the rapid bacteria kill times needed for pool treatment. However, at such high concentration levels, quaternary ammonium salts in general have the potential of producing objectionable, aesthetically unpleasing turbid swimming pool water having a high total organic carbon (TOC) content. Furthermore, such high concentrations of quaternary ammonium salts may increase the likelihood of skin irritation of people using those bathing facilities.

Quaternary ammonium salts have also been used in swimming pools, spas and hot tubs as algaecides. For example, known commercial algaecide products include SUN ® Algae Preventor (an alkyl dimethyl benzylammonium chloride) and HTH ® Non-Foaming Algaecide Concentrate [poly[oxyethylene(dimethyliminio)ethylene(dimethyliminio)ethylene dichloride]]. Such algaecides are used in relatively low concentrations (under 10 ppm by weight). At such concentrations, these known quaternary ammonium algaecides generally do not provide the rapid kill times for swimming pools.

In practice, harmful bacteria must be killed rapidly if they are present in a swimming pool, spa or hot tub. Indeed, the standard test method for disinfectants in swimming pools [American Organization of Analytical Chemists (A.O.A.C.) test method 4.047 entitled "Disinfectants (Water) for Swimming Pools"] requires that a swimming pool bactericide kills high levels of bacteria in only 30 seconds of contact. With quaternary ammonium salts, this rapid bactericidal activity must be accomplished at low concentrations, e.g. 60 ppm or less, to avoid the potential of producing objectional, unpleasing turbid swimming pool water having a high total organic carbon (TOC) content as well as increasing the likelihood of skin irritation of people using these bathing facilities.

It is believed that the present invention represents a viable alternative to the above-noted problems with existing swimming pool, spa and hot tub bactericides.

Examples of references describing the use of individual quaternary ammonium compounds or other water-treatment bactericides or combinations of bactericides for water treatment and other applications include:

U.S. Pat. No. 3,510,424, which issued to Zumbrunn on May 5, 1970, teaches that inorganic and organic peroxoacids such as peroxosulfuric acid and its salts and peroxodisulfuric acid and its salts may be used to convert toxic cyanides in industrial effluent streams to non-toxic and hydrolysable cyanates.

U.S. Pat. No. 3,567,729, which issued to Lewis et al. on Mar. 2, 1971, teaches the use of certain quaternary ammonium salts as germicides.

U.S. Pat. No. 3,624,082, which issued to Lewis et al. on Nov. 30, 1971, teaches a process for making selected quaternary ammonium salts which may be useful as germicides.

U.S. Pat. No. 3,702,298, which issued to Zsoidos et al. on Nov. 7, 1972, teaches a method of treating swimming pools with a combination of a peroxy salt, such as salts of peroxymonosulfuric acid, and a copper salt.

U.S. Pat. No. 3,730,702, which issued to Shay et al. on May 1, 1973, teaches a method of inhibiting microorganisms by applying thereto selected water-soluble unsymmetrical di-higher alkyl dimethyl ammonium salts. This product may be used to disinfect hard surfaces, fabrics, topical portions of the body and water.

U.S. Pat. No. 3,733,420, which issued to Wakeman et al. on May 18, 1973, teaches a method of inhibiting microorganisms in hard water aqueous solutions [e.g., swimming pools (see col. 3, line 15)] using octyl dodecyl dimethyl ammonium salts. It is noted that this invention is stated to be useful for bactericidal purposes (see col. 4, line 11).

U.S. Pat. No. 3,845,216, which issued to Brink et al. on Oct. 29, 1974, teaches a method of controlling the growth of bacteria in aqueous systems by contacting the system with a combination of B-bromo-B-nitrostyrene and didecyldimethyl ammonium chloride.

U.S. Pat. No. 4,098,602, which issued to Seymour et al. on Jul. 4, 1978, teaches an algicidal composition comprising selected ammonium quaternary compounds and a copper complex formed by reacting a water insoluble copper compound and alkanol amines.

U.S. Pat. No. 4,311,598, which issued to Verachtert on Jan. 19, 1982, describes a process for the disinfection of a bacteria-containing aqueous medium by contacting that medium with a combination of hydrogen peroxide or peroxyacid, a soluble copper salt and an autoxidisable reducing agent (e.g., 1,2,3-trihydroxybenzene, benzaldehyde, dihydroxyfumaric acid, malonic acid, ascorbic acid, or an alkali metal sulfate.

U.S. Pat. No. 4,450,174, which issued to Green et al. on May 22, 1984, describes the use of di-n-decyl dimethyl quaternary ammonium salts to inhibit bacteria in aqueous systems.

U.S. Pat. No. 4,594,091, which issued to Givan on Jun. 10, 1986, is directed to the use of certain boron derivatives to inhibit algal and fungal growth in water.

U.S. Pat. No. 4,790,940, which issued to Costaldi et al. on Dec. 13, 1988, teaches a process for the treatment of free cyanide-containing wastewater to destroy the free cyanide content thereof by treating said waters under alkaline conditions with polysulfide in the presence of a cationic surfactant catalyst (e.g., dialkyldimethyl quaternary ammonium salt).

U.S. Pat. No. 4,923,619, which issued to Legros on May 8, 1990, teaches the treatment of water of swimming pools and industrial water by means of a combination of (a) quaternary ammonium salts and (b) water-soluble copper and/or silver salts and peroxide compounds releasing oxygen, such as monopersulfate or peroxidisulfate of potassium. See col. 1 of this patent.

U.S. Pat. No. 4,952,398, which issued to Tapin on Aug. 28, 1990, teaches the treatment of swimming pool water using the combination of a quaternary ammonium compound and a copper salt as a biocide.

U.S. Pat. No. 5,131,938, which issued to Girvan on Jul. 21, 1992, suggests that certain boron derivatives may be used for killing algae and fungus in swimming pools. This patent further teaches that these boron derivatives may be used with known pool sanitizers (e.g., halogens, copper, hydrogen oxide, ozone, oxone, and quaternary ammonium compounds). See col. 5 of this patent.

U.S. Pat. No. 5,149,354, which issued to Delaney on Sep. 22, 1992, suggests a composition to inhibit the growth of algae, fungi, and bacteria, and to prevent the formation of turbidity in pool water comprising certain amounts of (a) copper sulfate, (b) silver nitrate, (c) sodium gluconate, (d) zinc chloride or zinc sulfate, (e) water, and (f) a complexone capable of forming water-soluble copper complexes (e.g., EDTA or a suitable alkali metal salt thereof).

United Kingdom Pat. Application 2,194,227, filed by Crystalclear S. A. and published on Mar. 2, 1988, teaches treating a body of water, such as a swimming pool, by adding thereto a liquid component and an oxidizing component. The liquid component comprises a polymeric cationic quaternary ammonium compound, a sequestering agent, and a copper salt. The oxidizing component may include sodium perborate, potassium persulfate, an alkali or alkaline earth hypochlorite, a trichloroisocyanurate, or an alkali metal dichloroisocyanurate.

European Pat. No. 59,978, which was granted to Bayrol on Jun. 13, 1984, claims a process for the disinfection of water and the oxidative decomposition of oxidizable impurities contained in the water by adding to the water the combination of (a) quaternary ammonium compounds, (b) water-soluble copper salts and or silver salts, and (c) an oxygen-liberating peroxide compound (e.g., potassium hydrogen monopersulfate).

European Pat. Application No. 0286453, which was filed by Pernox Manufacturing Company and published on Oct. 12, 1988, describes a biocidal composition for the treatment of water comprising certain quaternary ammonium compounds together with copper cations and/or a biocide containing a gem. halonitromethylene group.

G. R. Bhat et al. "The Green Hair Problem: A Preliminary Investigation", J. Soc. Cosmet. Chem. Vol. 30, 1–8 (January/February 1979) suggests that the combination of copper and peroxide enhances the phenomenon of blond hair acquiring a green tint. The experiments in this paper included a test where the blond hair was oxidized with hydrogen peroxide and immersed in a commercial formulation of a quaternary ammonium compound (distearyl dimethyl ammonium chloride).

L. K. Landeen et al. "Efficacy of Copper and Silver Ions and Reduced Levels of Free Chlorine in Inactivation of Legionella Pneumophila", Applied and Environmental Microbiology, Dec. 1989 pages 3045–3050, describes the activity of copper and silver ions in the presence of low levels of free chlorine against Legionella pneumophila.

M. T. Yahya "Disinfection of Bacteria in Water Systems by using Electrolytically Generated Copper:Silver and Reduced Levels of Free chlorine", Con. J. Microbiol. Vol. 36, pages 109–116, 1990, describes the activity of copper or silver ions with low levels of free chlorine against various bacteria in water.

G. P. Fitzgerald "Compatibility of Swimming Pool Algicides and Bactericides, Water & Sewage Works," vol. 115(2), pages 65–71 (1968), teaches that various amines, quaternary ammonium compounds, copper and silver salts have algistatic, algicidal, and bactericidal properties in swimming pools.

U.S. EPA Freedom of Information Request RIN-5973-92 shows that Bio-Guard MSA Algicide made by Bio-Lab, Inc. of Decatur, Ga. in 1974 contained the combination of copper and a quaternary ammonium compound (dimethyl dichlorobenzyl ammonium chloride).

Separately, di-isodecyl dimethyl ammonium chloride (sold commercially as BTC-99, by Stepan Co.) has been reported as having several uses.

Stepan Product Bulletin for BTC-99 (copyright 1990) states BTC-99 is useful as a microbiocide for swimming pool and cooling water treatment applications. A typical maintenance dose for a swimming pool is 3 oz. per 20,000 gallons. This brochure states that BTC-99 has demonstrated complete destruction of various algae including Green Algae, Square D Algae, Blue-Green Algae, and Black Algae.

BRIEF SUMMARY OF THE INVENTION

Accordingly, the present invention is directed to a process for sanitizing water in swimming pools, spas and hot tubs whereby the level of bacteria in said water is lowered comprising:

treating said water with a bactericidal effective amount of a combination of di-isodecyl dimethyl ammonium chloride and copper (II) ions, the concentration of di-isodecyl dimethyl ammonium chloride in said water being less than 60 parts per million parts of water (60 ppm) by weight; and treating said water at least intermittently with an oxidant selected from the group consisting of available chlorine, available bromine, and ozone.

DESCRIPTION OF PREFERRED EMBODIMENTS

The quaternary ammonium salt employed in the present invention, di-isodecyl dimethyl ammonium chloride, is a commercially available algaecide sold under the name BTC-99 by Stepan Chemical Co. of Northfield, Ill. Its Chemical Abstract Number (CAS) is 91490-94-7, and it is also known as isodecanamimium, N-isodecyl-N,N-dimethyl, chloride.

Various preparations of di-isodecyl dimethyl ammonium chloride are suggested in U.S. Pat. No. 4,444,790, which issued to Green et al. on Apr. 24, 1984.

The source of copper (II) ions used in the present invention may be any source of copper (II) cations including any water-soluble copper (II) salts which have a biocidally acceptable anion, which is capable of solubilizing copper (II) cations in water and is compatible with the above-noted quaternary ammonium salt. Examples of such copper (II) sources include copper (II) carbonate, copper (II) benzoate, copper (II) bicarbonate, copper (II) chloride, copper (II) sulfate, copper (II) bromide, copper (II) acetate, copper (II) formate, copper (II) trichloroacetate, copper (II) triethanolamine complex, copper (II) ethylenediamine tetraacetic acid complex, copper (II) citrate, copper (II) gluconate, and mixtures thereof. Copper (II) sources would also include any device, compound, or process which generates copper (II) ions in water. The preferred source of said copper (II) ions is copper (II) sulfate.

The present application recites "a bactericidal effective amount of the combination" of this quaternary ammonium salt and copper (II) ions. This term, as used in the present specification and claims, means any total amount of these two components which results in an effective bactericidal activity against at least 99.9% preferably 99.99% of bacteria initially present in the water treated with this combination.

In other words, if a body of water containing one million colony forming units (CFU's) of bacteria per milliliter was treated in accordance with the present invention, then less than 1,000 colony forming units (CFU's) will be left per milliliter of water after contact with this combination. Preferably, it is also desired that this amount of this combination be sufficient to cause a rapid decrease or lowering of the bacteria within about 60 seconds from contact, more preferably within about 30 seconds, so as to meet the requirements of the above-noted standard test method for disinfectants in swimming pools (A.O.A.C. Test Method 4.047).

The preferred weight ratio of the quaternary ammonium salt to the copper (II) ion source is from 3:1 to 600:1, more preferably, from about 30:1 to about 300:1, most preferably, from about 60:1 to about 150:1.

The quaternary ammonium salt and copper (II) ion source may be combined in any conventional way. Preferably, it may be desirable to simply mix them together for later addition to a swimming pool, spa or hot tub.

Other conventional water-treatment chemicals may be contained with these two critical chemicals. Such conventional chemicals may include defoamers, perfumes, insect repellants, flocculants, dyes, colorants, and sequestering agents.

Alternatively, the di-isodecyl dimethyl ammonium chloride and copper (II) ion source may be added individually to the water of the swimming pool, spa or hot tub. Such additions may be simultaneously or at different times. If the latter method is employed, such additions of second component are preferably made before the concentration of the first component becomes negligible (i.e., less then 0.01 ppm).

It should be noted that the maximum concentration of di-isodecyl dimethyl ammonium chloride in the water being treated should be about 60 ppm by weight. This maximum limit is necessary to avoid the potential of producing objectionable, aesthetically unpleasing turbid water having a high total organic carbon (TOC) content and to decrease the likelihood of any skin irritation of bathers using these facilities. The preferred concentration of this quaternary ammonium salt in the water is from about 5–40 ppm by weight. It is also preferred that the concentration of the copper (II) ion in the water be from about 0.1–2 ppm by weight, more preferably about 0.5–1 ppm by weight. These levels are desired to cause a decrease of at least 99.9%, preferably 99.99%, of bacteria in the water, more preferably, within 30 seconds.

In the present invention, a pool operator would only want to dissolve the quaternary ammonium compound and copper (II) ion source in the water being treated and ensure that a uniform concentration of each in the above ranges is achieved.

Depending upon the particular aqueous medium being treated and upon various external factors, redosing of the quaternary ammonium salt and copper (II) ions may be necessary. For example, a heavily used swimming pool may require redosing at more frequent intervals than another pool of the same size which was used only occasionally or lightly. Redosing of the quaternary ammonium salt and copper (II) ion source may be carried out together or individually. Pool operators may use standard testing kits to determine the concentration of each component and whether or not (and how much) redosing is needed.

A critical feature of the present invention is to add at least intermittently an oxidant selected from the group consisting of available chlorine, available bromine, and ozone to the water along with the combination of the quaternary ammonium salt and copper (II) ions. The terms "available chlorine" and "available bromine" as used in the present specification and claims are intended to mean positive chlorine and positive bromine as it is well known in this art. Available chlorine sources include chlorine ($Cl_2$) calcium hypochlorite, chlorinated isocyanurates, chlorinated glycolurils, chlorinated hydantoins, chlorinated imidazolidinones, chlorinated oxazolidinones, chlorinated amines and mixtures thereof.

Available bromine sources include liquid bromine, nitrogen-bound bromine such as the bromohydantoins (e.g., 1-bromo-3-chloro-5,5-dimethylhydantoin), bromide ion combined with oxidizers such as ozone, potassium monoperoxysulfate, or a chlorine source and bromide ion converted by electrolytic generation.

Ozone sources include ozone which is generated from oxygen or air through use of a corona discharge generator or a UV light generator (photolytically).

Generally, it is desired to add the oxidant source at intervals to effect a "shock treatment" on the body of water being treated. The desired concentration of available chlorine being added will depend upon the particular available chlorine source chemical being employed and the specific application required. Usually, it is desirable to add about 0.5 to about 30 ppm, more preferably, about 2–15 ppm by weight of available chlorine to the water at least once every thirty days, preferably at least once every 4–10 days.

The desired concentration of available bromine being added is similar to that of available chlorine. More preferably, one would add about 0.5 ppm to about 30 ppm, most preferably about 2–15 ppm, of available bromine to the water at least once every 30 days, preferably at least once every 4–10 days.

The desired concentration of ozone being added should be such that the ozone level in the water will meet the required oxidant demand for that particular application. Generally, that minimum amount of ozone added is sufficient to result in at least 0.1 mg/liter residual ozone at the discharge into the pool. The preferred amount of ozone generated may be controlled and monitored at the outlet of the ozone contact chamber by means of redox potential (oxidation-reduction potential in North America=ORP), rather than by monitoring for residual ozone. Pools and spas which use ozone alone are generally maintained at ORP level of 720±20 mV. This normal level may change because of the amount of oxidizable material in the water. The preferred maximum level of ozone addition should be less than that which would cause discomfort to humans.

By practice of the present invention, one is able to rapidly and economically sanitize water in swimming pools, spas and hot tubs to safe and acceptable bacteria levels. Furthermore, at the very low concentrations found to be effective, the particular quaternary ammonium compound is believed to have no effect on the eyes, no significant objectionable odor or taste, and does not significantly bleach clothing as may happen with the use of chlorine or ozone. Furthermore, this invention is believed effective against bacteria resistant to the use of di-isodecyl dimethyl ammonium chloride or copper (II) ions alone or the combination thereof.

Still further, this invention is believed effective against bacteria resistant to the use of di-isodecyl dimethyl ammonium chloride or chlorine shock or the combination thereof. In other words, prolonged treatment of water in a swimming pool, spa, or hot tub with only one or any two of three components of the present invention may result in the growth of resistant bacteria whereas the use of all three components of the present invention would prevent the development of such resistant bacteria. The use of this particular quaternary ammonium salt in the present invention causes little foaming and results in clear water compared to many other quaternary ammonium salts.

The following experiments are provided to better understand the present invention. All parts and percentages are by weight except where explicitly stated otherwise. All temperatures are degrees Celsius (°C.) except where explicitly stated otherwise.

I. Laboratory Testing Vs. *E. Coli* Bacteria

A. Inoculum Preparation

*E. coli*, ATCC 11229, were grown on tryptic soy agar slants for 18 to 24 hours at 35° C. The slants were then washed with 10 ml of sterile saline (0.85% by weight NaCl) and centrifuged at 10,000 revolutions per minute for 10 minutes. The supernatant was discarded, and the culture resuspended in 10 ml of sterile saline (0.85%). The centrifugation and removal-of-supernatant steps were repeated two times. The culture was then resuspended in sterile reverse osmosis water, and the culture suspension adjusted to an optical density of 0.2 at 550 nm using a Bausch & Lomb colormeter, Model No. 20. The final culture suspension has approximately 200,000,000 viable cells per milliliter, i.e., 200,000,000 colony forming units/ml or 200,000,000 cfu/ml.

B. Preparation of Test Solutions

The test used herein as a standard to verify and demonstrate the bactericidal activity of the present invention is a variation of the American Organization of Analytical Chemists (A.O.A.C.) procedure 4.047 entitled "Disinfectants (Water) for Swimming Pools". The variation, which makes the test more stringent, consists of using dechlorinated tapwater, having an alkalinity of 100 ppm and a calcium hardness of 90–100 ppm. The quaternary ammonium salt solutions were prepared at the use concentrations given in Table I at pH 7.5. A stock copper (II) solution was prepared at 100-fold the test concentration from copper sulfate pentahydrate at pH 5.5. A stock oxidizer solution was prepared at 100 times the test concentration from OXONE potassium peroxymonosulfate with the solution having a pH of 7.5.

C. Bactericidal Efficacy Testing

The quaternary ammonium salt, copper (II), and OXONE potassium peroxymonosulfate were evaluated at the concentrations set forth in Table I either by themselves or in the indicated combinations. For tests involving individual components, 10 ml of the appropriate solution or sterile reverse osmosis water were added aseptically to sterile, capped culture tubes. For tests involving combinations of ingredients, 10 ml of the quaternary ammonium salt solutions were added aseptically to sterile, capped culture tubes and an appropriate volume of copper (II) or the OXONE monopersulfate compound stock solution added less than 5 minutes before the addition of the culture suspension to start the timed exposure.

To the above-described test solutions, at room temperature, 50 microliters of bacterial suspension were added, and the time-of-addition recorded as zero time. Immediately after adding the bacteria suspension, the reaction mixture was vortexed for 10 seconds, and 1 milliliter samples taken at times shown in Table I. Just prior to sampling, the vortexing procedure was repeated. Each 1 milliliter sample was added immediately to 9 ml of a neutralizer. The neutralizer (pH of 7.5) was made by combining (a) 33.4 milliliters of an aqueous solution containing 4% by weight azolectin and 28% by weight TWEEN ® 80; (b) 8.33 milliliters of a standard phosphate buffer; and (c) 558.33 milliliters of distilled water to make a 600 milliliter stock neutralizer solution. This solution was autoclaved for 20 minutes at 121° C. to kill any organisms therein. A second stock neutralizer solution was similarly prepared for those tests in which copper (II) was or OXONE would be present. This second neutralizer stock was prepared the same way except 0.6 grams of sodium thiosulfate and 0.6 grams of sodium thioglycolate were added to the 600 milliliter solution before autoclaving. Controls were run to insure that compounds are effectively neutralized. About 1,000,000 cfu/ml of the test bacteria were exposed to each test solutions.

After neutralization at the selected time-of-contact, 1 milliliter portions of the neutralized samples were added to plastic petri dishes, and tempered tryptone glucose extract agar added to each plate. The plates were then incubated at 37° C. for about hours and colonies were counted. The numbers are then corrected to cfu/ml by applying the appropriate dilution factor used.

TABLE I

LAB TEST vs. E. COLI BACTERIA

| BTC-99** | OXONE | $CU^{+2}$ | E. COLI REMAINING (cfu/ml)* | |
|---|---|---|---|---|
| (ppm) | (ppm) | (ppm) | 0.5 min. | 5.0 min. |
| 40 | 0 | 0 | 1925 | 350 |
| 20 | 0 | 0 | >3000 | 280 |
| 10 | 0 | 0 | >3000 | >3000 |
| 0 | 12 | 0 | >3000 | >3000 |
| 0 | 24 | 0 | >3000 | >3000 |
| 0 | 0 | 1 | >3000 | >3000 |
| 0 | 24 | 1 | >3000 | >3000 |
| 20 | 0 | 1 | >3000 | >3000 |
| 20 | 12 | 0 | >3000 | 1400 |
| 20 | 12 | 1 | >3000 | >3000 |
| 10 | 0 | 0.5 | >3000 | >3000 |
| 10 | 12 | 0 | >3000 | >3000 |
| 10 | 12 | 0.5 | >3000 | >3000 |

*At "0" time, approximately 1,000,000 cfu/ml
**ppm of active ingredient

D. Conclusions

TABLE I shows the laboratory data for testing di-isodecyl dimethyl ammonium chloride at 10 to 40 ppm active ingredient as a potential sanitizer in a swimming pool, hot tub, or spa. By itself, this quaternary ammonium salt is completely ineffective at 10 ppm, even after a 5-minute contact-time. At 20 ppm, efficacy is poor at 30-seconds contact-time, and a significant number of bacteria survivors is left after 5 minutes contact-time. At 40 ppm, bactericidal efficacy is only 99.8% at a 30-second contact-time. Thus, it is concluded that di-isodecyl dimethyl ammonium chloride is ineffective by itself for use as sanitizer for these applications.

Also shown is the laboratory data for testing the swimming pool, hot tub, and spa shock-treatment oxidant, OXONE potassium peroxymonosulfate compound at 12 and 24 ppm, and for testing copper (II) at 1 ppm. By themselves, neither is an effective bactericide.

Combining copper (II) and OXONE does not improve the bactericidal efficacy. Combining di-isodecyl dimethyl ammonium chloride with either copper (II) or OXONE or a mixture of copper (II) and OXONE was found to actually decrease the bactericidal activity as compared to using only di-isodecyl dimethyl ammonium chloride. Thus, it is concluded that combinations of this quaternary ammonium salt with copper (II) and/or an OXONE shock treatment is ineffective for use as a sanitizer for these applications.

II. Swimming Pool Tests

A. Test Pools

Comparative test were performed in pools having a water capacity of about 2,100 gallons. The pools were filled with water and the alkalinity adjusted to about 100 ppm, and the calcium hardness adjusted to about 200 ppm using standard swimming pool chemicals. The pH was adjusted to about 7.5 initially and maintained at pH 7-8. Each swimming pool was equipped with a standard sand filter through which the pool water circulated for 8 hours per day. Bacteria counts were determined by standard methods using 2 and/or 7-day incubation times.

B. Di-isodecyl Dimethyl Ammonium Chloride/OXONE; Swimming Pool Test System-1

To the above-described pool 1 was added 688 ml of BTC-99, corresponding to a swimming pool concentration of 40 ppm di-isodecyl dimethyl ammonium chloride. OXONE potassium peroxymonosulfate compound was added at 12 ppm as an oxidant shock treatment. A protocol was followed so that the quaternary ammonium salt concentration was maintained at 30-40 ppm for the test duration. An algae suspension containing about 6 billion associated bacteria cells was added on days 6, 13, 20, and 27 after collecting a water sample for determining bacteria counts. OXONE potassium peroxymonosulfate compound was added at 21 ppm on days 8, 15, and 22. A synthetic bather load was added 5 days a week to simulate typical compounds introduced to a pool from bathers.

TABLE II shows bacteria counts at various times during the 1-month test for this system. As predicted from the laboratory tests, the use of di-isodecyl dimethyl ammonium chloride with an oxidant shock treatment of OXONE potassium peroxymonosulfate compound failed to effectively prevent the growth of bacteria.

TABLE II

DI-ISODECYL DIMETHYL AMMONIUM CHLORIDE/ OXONE; SWIMMING POOL TEST SYSTEM-1

| | BACTERIA COUNTS (cfu/ml) | |
|---|---|---|
| DAY | 2 DAYS | 7 DAYS |
| 1 | 0 | — |
| 2 | 0 | 0 |
| 6 | 610 | 510 |
| 7 | 7500 | 8900 |
| 9 | — | 0 |
| 13 | 32 | 34 |
| 14 | 120,000 | 120,000 |
| 16 | — | 0 |
| 20 | — | 54 |
| 21 | — | 83,000 |
| 23 | — | 0 |
| 27 | 21,000 | — |
| 28 | 820,000 | 760,000 |

C. Di-isodecyl Dimethyl Ammonium Chloride/Chlorine; Swimming Pool Test System-2

This test was performed analogously to that described in Section II-B, with the exception that the initial and weekly oxidant shock treatment employed 7.5 ppm free available chlorine using 65% calcium hypochlorite. Oxidant was added on days 8, 15, 22 and 29; algae, on days 6, 13, 20, 27 and 34; synthetic bather load, 5 days a week.

Table III shows bacteria counts at various times during the 35-day test. Relatively low bacteria counts were found up to day 28, at which time a high bacteria count of about 735 cfu/ml was recorded. By day 34 the bacteria count, before algae/bacteria addition, had increased to 12,000 cfu/ml. Thus, as is obvious, di-isodecyl dimethyl ammonium chloride with an oxidant shock treatment of free available chlorine failed to effectively prevent the growth of bacteria.

TABLE III

DI-ISODECYL DIMETHYL AMMONIUM CHLORIDE/ CHLORINE; SWIMMING POOL TEST SYSTEM-2

| DAY | BACTERIA COUNTS (cfu/ml) | |
|---|---|---|
| | 2 DAYS | 7 DAYS |
| 1 | 0 | 0 |
| 2 | 0 | 0 |
| 6 | 0 | 2 |
| 7 | 9 | 14 |
| 9 | — | 0 |
| 13 | 0 | 0 |
| 14 | 13 | 16 |
| 16 | — | 0 |
| 20 | — | 54 |
| 21 | — | 22 |
| 23 | — | 0 |
| 27 | 69 | 48 |
| 28 | 760 | 710 |
| 30 | — | 0 |
| 34 | 12,000 | — |
| 35 | 7,200 | — |

Effect of Copper (II) on a Di-isodecyl Dimethyl Ammonium Chloride/Chlorine System; Swimming Pool Test System-3

On day 29 Pool Test 1, described in Section II-B, was modified to Pool Test 1a by using an oxidant shock treatment of 7.5 ppm free available chlorine in place of the OXONE potassium peroxymonosulfate compound shock treatment. On day 30, the bacteria count was 0 cfu/ml, but by day 34, the bacteria count had increased to 1,100,000 cfu/ml. The algae suspension containing bacteria was added on day 34, and on day 35 a bacteria count of 3,100,000 cfu/ml was found. These data confirmed the ineffectiveness of a di-isodecyl dimethyl ammonium chloride/chlorine system for controlling bacteria, as concluded by the test described in Section II-C.

On day 36, pools 1a and 2, were oxidant shock treated with 15 ppm free available chlorine. On day 38, bacteria counts in both pools were <1 cfu/ml, and 1 ppm copper (II) was added to pool 1; no copper (II) was added to pool 2. On day 42, the bacteria count in the copper (II) treated pool 1a was 15 cfu/ml, but was 4500 cfu/ml in pool 2 that was not treated with copper (II). It is thus obvious that effective bacteria control was achieved by using a di-isodecyl dimethyl ammonium chloride/copper (II) system with a chlorine oxidant shock treatment.

Additional confirmation of the exceptional bactericidal efficacy of this system was found by removing a sample of pool water on day 36 from pool 2, prior to shock treatment, and adding 1 ppm copper (II) to it. At the start of this confirmation test the bacteria count was 22,000 cfu/ml; 90 minutes after contact with the copper (II), the bacteria count had dropped to the detection limit of less than 1 cfu/ml.

E. Di-isodecyl Dimethyl Ammonium Chloride/Copper (II)/OXONE; Swimming Pool Test System-4

To test pool 4, as described in Section II-A, was added 344 ml of BTC-99, corresponding to a swimming pool concentration of 20 ppm di-isodecyl dimethyl ammonium chloride. This was followed by the addition of 170 ml of an 18% copper sulfate pentahydrate solution, corresponding to 1 ppm copper (II) in the swimming pool. OXONE potassium peroxymonosulfate compound was added at 12 ppm as an oxidant shock treatment on Day 8. Bacteria counts were monitored for 33 days from the initial charge of the quaternary ammonium salt, which was periodically added to maintain a concentration of about 20 ppm. The highest count was only 29 cfu/ml during this time.

On day 34, an algae suspension containing bacteria (approximately 25 billion cells) was added. This addition was repeated every 7 days for the duration of the test. On day 36, 12 ppm OXONE potassium peroxymonosulfate compound was added. This addition was repeated every 7 days to day 71, at which time the addition of 24 ppm OXONE potassium peroxymonosulfate compound every 7 days commenced. A synthetic bather load was added 5 times a week starting on day 34 of the test.

TABLE IV shows the bacteria counts at various times during the 83-day test. As predicted from the laboratory tests, the use of di-isodecyl dimethyl ammonium chloride with copper (II) and OXONE potassium peroxymonosulfate compound oxidant shock treatment failed to effectively control the growth of bacteria.

TABLE IV

DI-ISODECYL DIMETHYL AMMONIUM CHLORIDE/ COPPER (II)/OXONE; SWIMMING POOL TEST SYSTEM-4

| DAY | BACTERIA COUNTS (cfu/ml) | |
|---|---|---|
| | 2 DAYS | 7 DAYS |
| 1 | — | 0 |
| 2 | — | 0 |
| 7 | — | 1 |
| 14 | 0 | 29 |
| 21 | — | 0 |
| 28 | — | 4 |
| 30 | — | 0 |
| 35 | — | 13 |
| 42 | — | 580 |
| 44 | — | 1 |
| 49 | — | 1600 |
| 51 | — | 3 |
| 56 | — | >3000 |
| 57 | 470,000 | 560,000 |
| 58 | 0 | 0 |
| 59 | 1000 | 690 |
| 62 | 10,000 | 10,000 |
| 69 | 1,200 | 1,000 |
| 71 | — | 31,000 |
| 76 | 136 | 139 |
| 77 | 4,500 | 5,700 |
| 78 | 140,000 | 130,000 |
| 79 | 0 | 0 |
| 80 | 3 | 4 |
| 83 | 20,000 | 20,000 |

III. GENERAL CONCLUSIONS

Laboratory tests using di-isodecyl dimethyl ammonium chloride lead one to conclude that this compound is an ineffective bactericide for use as a sanitizer in swimming pools, hot tubs, and spas when used alone, or in combination with copper (II) or an oxidant shock treatment. This general conclusion was confirmed by tests in swimming pools, with the unexpected exception that, when di-isodecyl dimethyl ammonium chloride was used with copper (II) in conjunction with chlorine as an oxidant shock treatment, a superior sanitizing system resulted as compared to the use of a similar system with OXONE potassium peroxymonosulfate compound for oxidant shock treatment.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A process for sanitizing water in swimming pools, spas, and hot tubs whereby the level of bacteria in said water is lowered comprising:

treating said water with a bactericidal effective amount of a combination of di-isodecyl dimethyl ammonium chloride and copper (II) ions, the concentration of di-isodecyl dimethyl ammonium chloride in said water being less than about 60 parts per million parts of water by weight; and treating said water at least intermittently with an oxidant selected from the group consisting of available chlorine and ozone; wherein if said oxidant is available chlorine, then about 0.5 to about 30 ppm by weight of said available chlorine is added to said water at least once every thirty days; and wherein if said oxidant is ozone, then the amount of ozone added to the water is sufficient to meet the required oxidant demand for said water and is sufficient to result in at least 0.1 mg/liter residual ozone at the ozone discharge into said water.

2. The process of claim 1 wherein about 2–15 ppm by weight of said available chlorine is added to the water.

3. The process of claim 2 wherein said available chlorine is added every 4–10 days.

4. The process of claim 1 wherein said oxidant is ozone.

5. The process of claim 1 wherein the source of said copper (II) ions is selected from the group consisting of copper (II) carbonate, copper (II) benzoate, copper (II) bicarbonate, copper (II) chloride, copper (II) sulfate, copper (II) bromide, copper (II) acetate, copper (II) formate, copper (II) trichloroacetate, copper (II) triethanolamine complex, copper (II) ethylenediamine tetraacetic acid complex, copper (II) citrate, copper (II) gluconate, and mixtures thereof.

6. The process of claim 5 wherein the source of said copper (II) ions is copper (II) sulfate.

7. The process of claim 1 wherein the concentration of said di-isodecyl dimethyl ammonium chloride is maintained at about 5 to about 40 ppm by weight.

8. The process of claim 1 wherein the concentration of said copper (II) ions is maintained at about 0.1 to about 2 ppm by weight.

9. The process of claim 1 wherein said oxidant is available chlorine.

10. The process of claim 9 wherein the source of said available chloride is selected from the group consisting of chlorine ($Cl_2$), calcium hypochlorite, chlorinated isocyanurates, chlorinated glycolurils, chlorinated hydantoins, chlorinated imidazolidinones, chlorinated oxazolidinones, chlorinated amines and mixtures thereof.

* * * * *